(12) United States Patent
Katsuyama et al.

(10) Patent No.: US 6,242,092 B1
(45) Date of Patent: Jun. 5, 2001

(54) ZINC OXIDE-COATED MATERIAL AND FATTY ACID-SOLIDIFYING POWDER AND EXTERNAL PREPARATION FOR SKIN EACH MADE BY USING THE MATERIAL

(75) Inventors: Tomoyuki Katsuyama; Asa Kimura; Naoko Watanabe, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 08/945,210
(22) PCT Filed: Feb. 21, 1997
(86) PCT No.: PCT/JP97/00478
  § 371 Date: Dec. 29, 1998
  § 102(e) Date: Dec. 29, 1998
(87) PCT Pub. No.: WO97/31068
  PCT Pub. Date: Aug. 28, 1997

(30) Foreign Application Priority Data

Feb. 21, 1996 (JP) ................................... 8-060197

(51) Int. Cl.$^7$ .................................................. B32B 5/16
(52) U.S. Cl. ........................ 428/363; 428/403; 428/689; 428/702
(58) Field of Search .................. 424/401, 63; 518/844; 428/403

(56) References Cited

U.S. PATENT DOCUMENTS 3,087,828 * 4/1963 Linton .................................. 106/417
4,207,377 6/1980 Kindrick .

FOREIGN PATENT DOCUMENTS

| 58-52651 | * | 3/1983 | (JP) | ................ | C23C/11/08 |
| 8-32094 | * | 2/1996 | (JP) | ................ | H01L/31/04 |
| WO 94/01498 | | 1/1994 | (WO) . | | |

OTHER PUBLICATIONS

Derwent Publications Ltd., London, GB, AN 93–071009, Tayca Corp., "Flaky pigment compsn. for high dispersibility in cosmetic material—prepd by coating surface of flaky pigment with titanium oxide and coating with zinc oxide, for ultraviolet A beam shielding.".

Derwent Publications Ltd., London, GB, An 93–232556, Teika KK, Flaky pigment compsn. for cosmetics with low surface gloss—comprises flake surface coated titanium oxide or titanium–zinc composite oxide and zinc oxide.

* cited by examiner

*Primary Examiner*—William Krynski
*Assistant Examiner*—B. Shewareged
(74) *Attorney, Agent, or Firm*—Snider & Associates; Ronald R. Snider

(57) ABSTRACT

An object of the present invention is to provide a powder and an external preparation for skin using the same which has good spreadability and does not spoil fatty acid-solidity ability of zinc oxide.

A zinc oxide-coated material characterized as coating an amorphous state of zinc oxide on a substrate.

13 Claims, 6 Drawing Sheets

ZINC OXIDE-COATED MATERIAL AND FATTY ACID-SOLIDIFYING POWDER AND EXTERNAL PREPARATION FOR SKIN EACH MADE BY USING THE MATERIAL

THIS INVENTION CLAIMS THE PRIORITY OF JAPANESE PATENT APPLICATION NO. HEISEI 8-60197, FILED FEB. 21, 1996, WHICH IS INCORPORATED HEREIN BY REFERENCE.

TECHNICAL FIELD

The present invention relates to a zinc oxide-coated material and in particular, relates to the improvement of its fatty acid-solidifying ability.

BACKGROUND ART

Sebum is always eliminated from human skim Sebum gives horny layer moisture and flexibility, and further prevents inrush of injurious material and bacteria from outside and discharge of the material such as water from body, in the human skin which is normally kematinized.

However, sebum causes cosmetics which are applied on the skin to be fallen off the skin, a so-called cosmetic crumbling effect Sebum also causes oily gloss on the skin.

Various methods have been used for controlling the action of sebum on the skin. For example, kaolin, calcium carbonate, magnesium carbonate, and the like are excellent in absorbing perspiration or sebum. Further, powders, such as porous globular silicic anhydride, porous cellulose powder, and the like, which have sebum absorptivity are used.

Among these powders, zinc white, in particular, has sebum solidifying ability. It can effectively prevent cosmetic crumbling.

However, zinc oxide has a fault which is inferior in spreadability.

The coefficient of friction of zinc oxide is about 0.60, which is considerably high as compared with other powders used in cosmetics. Accordingly, the spreadability and usability of cosmetics are remarkably lower in the case where a large amount of zinc oxide is compounded.

The present inventors are planning the improvement of the spreadability by separating zinc oxide on fine flake powder such as mica.

However, the inventors has faced with the problem that the sebum-solidifying ability of zinc oxide disappears, in the case where zinc oxide is separated on mica and the like.

DISCLOSURE OF INVENTION

In view of the above-mentioned problems in the prior art, an object of the present invention is to provide a powder and an external preparation for skin using the same which has good spreadability without spoiling fatty acid-solidifying ability of zinc oxide-coated material.

As a result of diligent studies by the inventors for attaining the above-mentioned objects, the inventors found that the usability of zinc oxide can be improved without spoiling fatty acid-solidifying ability by separating zinc oxide on a substrate with specific separation form Accordingly, the present invention has been accomplished.

Namely, a zinc oxide-coated material in accordance with the present invention is characterized in that an amorphous state of zinc oxide is coated on a substrate.

Preferably, the substrate is a fine flake.

Preferably, the fine flake is mica.

Preferably, the fine flake is titanium oxide coated mica.

Preferably, the fine flake is iron oxide-coated titanium oxide coated mica.

Preferably, the amount of zinc oxide is in the range of 1 to 8%.

A fatty acid-solidifying powder in accordance with the present invention is composed of a zinc oxide-coated material.

An external preparation for skin in accordance with the present invention is compounded with a fatty acid& solidifying powder.

A process for manufacturing a zinc oxide-coated material in accordance with the present invention comprises mixing a substrate in zinc halide water solution which is adjusted pH 11 to 13 and separating zinc oxide generated by hydrolyzing zinc halide on the substrate.

In addition, in said process for manufacturing the zinc oxide-coated material, it is preferable that the separation of zinc oxide from the substrate is conducted by adding zinc halide or alkaline water solution to the water solution where the substrate is dispersed, to adjust pH to the prescribed value of 11 to 13.

BEST MODE FOR CARRYING OUT THE INVENTION

In the following, the preferable embodiments of the present invention are explained in connection with the drawings.

Synthesis of Zinc Oxide and Iron Oxide-Coated Titanium Oxide Coated Mica

Figure 1:
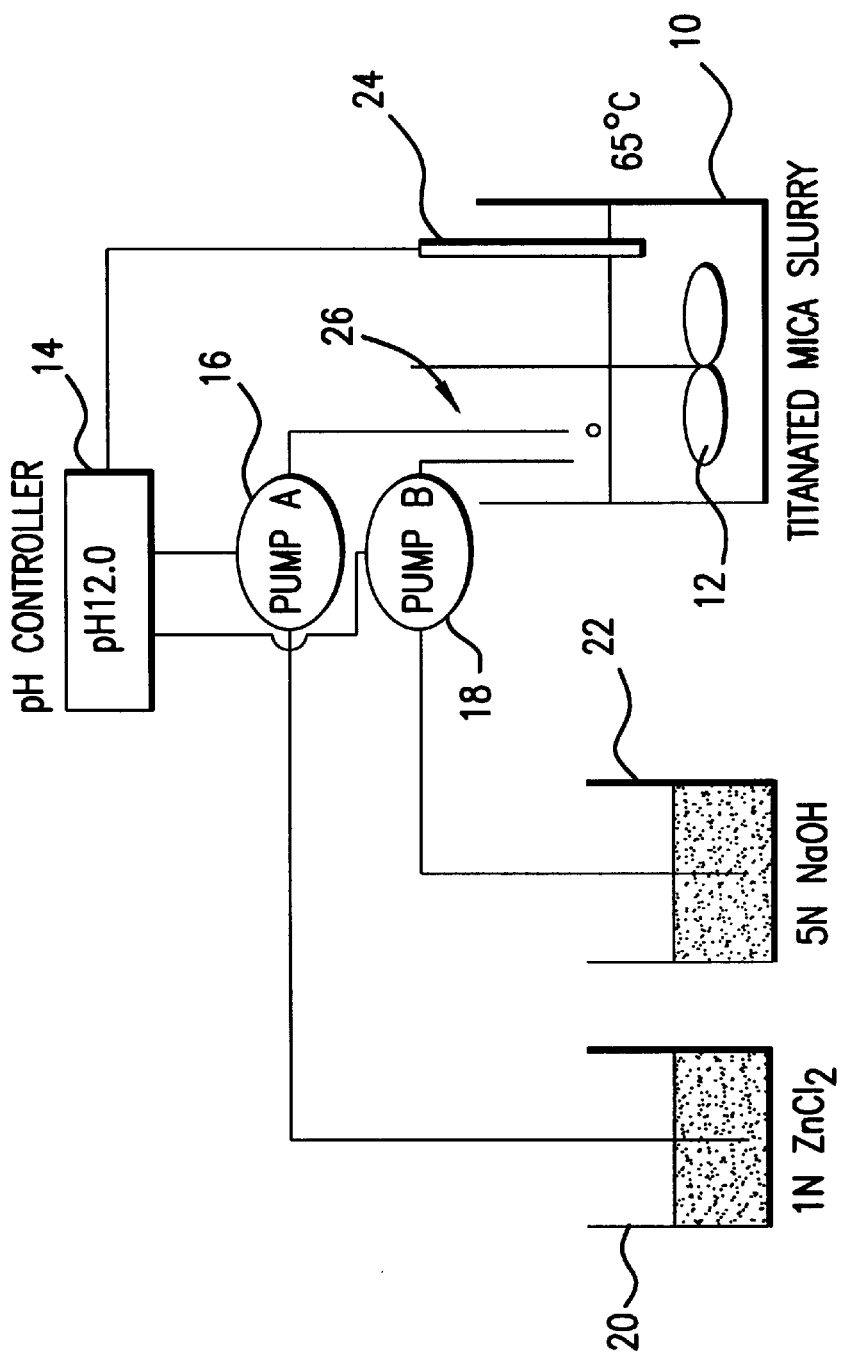
FIG. 1 is an explanatory view of a synthesizing device of zinc oxide and iron oxide-coated titanium oxide coated mica in accordance with one embodiment of the present invention.

First, a manufacturing example of a zinc oxide-coated powder in accordance with one embodiment of the present invention is explained according to FIG. 1. In the present embodiment, the amount of zinc oxide coated is 3% and that of iron oxide is 0.5%.

As shown in FIG. 1, 100 g of titanium dioxide-coated mica (red interference color, manufactured by Merck Corp.) was added to 3 liter separable round bottom flask 10. Then, to make an iron oxide-coated titanated mica 1.69 g of ferric chloride (hexahydrate) and 2.26 g of urea were added and dissolved in 1000 ml of clean water. A vaned stirring rod 12 which was connected to a motor is attached to the center of a cap and a reflux pipe (not shown in the drawing) was attached to the outside of the cap. The mixture was heated by a mantle heater with stirring. After continuously refluxing for 2 hours from the start of reflux, the heating was stopped and the cap was removed. The vaned stirring rod 12 and a thermometer were introduced to the slurry solution and the solution was cooled down to 65° C. under stirling at room temperature. After this, the solution was maintained at 65° C. by adjusting a heater and under stirring wherein titanium oxide coated mica flakes were coated with iron oxide. A pair of peristaltic pumps 16 and 18 were connected to a pH controller 14. The pH controller 14 was predetermined that the peristaltic pump 16 worked in the case where pH of the solution was 12 or more and the peristaltic pump 18 worked in the case where pH of the solution was less than 12. 1N $ZnCl_2$ 20 was connected to the peristaltic pump 16 and 5N NaOH 22 was connected to the peristaltic pump 18. Each peristaltic pump 16 and 18 was pre-adjusted to a flow velocity about 3 ml/min. A pH electrode 24 was introduced to the solution. A discharging portion 26 of the peristaltic pump tube was located on the surface of the solution The pH controller 14 and the peristaltic pumps 16 and 18 were operated. The operation of each peristaltic pump 16 and 18, and stirring were stopped at the point of time when 37 ml of 1N $ZnCl_2$ was added. A powder was removed by suction filtration of the powder slurry. After adding more than 1 liter of clean water and water washing, the powder was sucked and filtered again. After this, this water washing procedure was repeated twice. The obtained powder was dried for 12 hours at 150° C. Then, zinc oxide and iron oxide-coated titanium oxide coated mica was obtained.

In the following, the zinc oxide and iron oxide-coated titanium oxide coated mica manufactured as like the above-mentioned example 1 was evaluated.

The various evaluation methods are shown in the following.

Fatty Acid-Solidifying Ability

Taking 5 g of powder in 100 ml of a polypropylene container, 20 g of oleic acid was added to it. The mixture was mixed about 30 seconds by a disper.

After mixing, hardness was measured at thirteen minutes apart. Rheoner (RE3305, Yamaden) was used for measuring hardness. Hardness was found as the load (g/0.5 mm) that a cylinder of 8 mm diameter was inserted at the velocity of 0.5 mm/sec.

Gross Evaluation

Taking 1 g of powder in 100 ml of a polypropylene container, 15 g of nitrocellulose (citron, Musashi Toryo) was added to it. The mixture was mixed about 30 seconds by a disper. The obtained slurry was coated on a black paper by using an applicator with 0.101 mm clearance. After dried naturally, gonio-spectral reflectance of the coated-material was measured by GCMS-3 Murakami Color). The reflectance was measured under the conditions where the incident angle was fixed to −45° and the light receiving angle was in the range from −25° to 65°. The reflectance in each wavelength was used as the relative value of the reflectance of white standard plate (incident angle −45°, light receiving angle 0°), which was converted to luminance (Y value).

Interference Color

The above-mentioned coated material was measured by a colorimeter of CM100 Minolta). The colorimetric value was determined by Lab.

SEM Observation

The powder was mounted on the stage and was coated by platinum, then it was observed by a scanning electron microscope (S-450, Hitachi).

The Relationship of pH and Crystal Structure at Manufacturing Time of Zinc Oxide and Iron Oxide-Coated Titanium Oxide Coated Mica First, the present inventors conducted various studies concerning the process for manufacturing zinc oxide and iron oxide-coated titanium oxide coated mica because they have found that the fatty acid-solidifying ability was entirely disappeared when zinc oxide was coated on mica and the like using a general method. As a result, the present inventors found that pH during the manufacturing process has a great influence on the crystal structure of zinc oxide on mica. Also, they found that the difference of the crystal structure of zinc oxide has a great effect on fatty acid-solidifying ability.

Figure 2A:
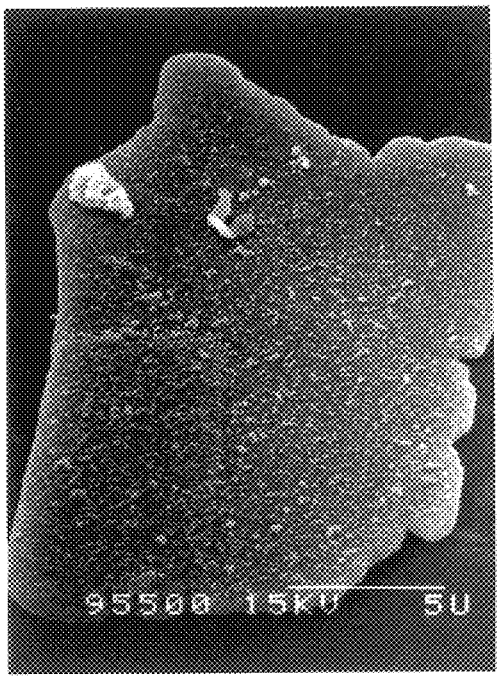
FIG. 2 contains microphotographs of amorphous state of zinc oxide and iron oxide-coated titanium oxide coated mica, FIG. 2 (A) shows a whole particle and FIG. 2 (B) shows the surface state which is further magnified.
Figure 2B:
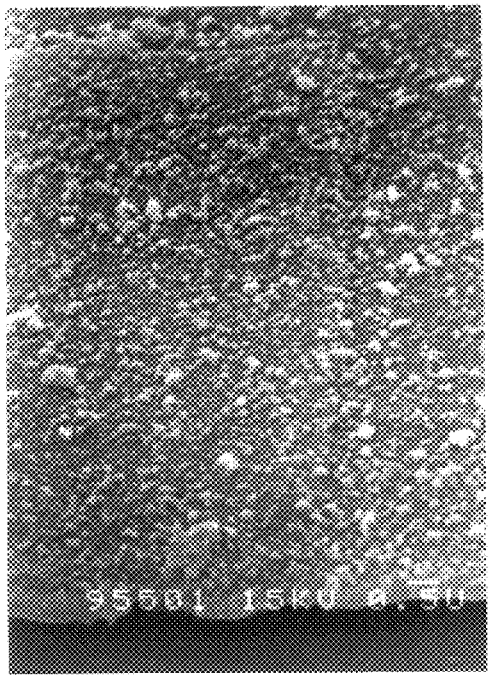

Microphotographs of zinc oxide and iron oxide-coated titanium oxide coated mica obtained with adjusting the pH of the solution at 12 by the pH controller 14 according to the above-mentioned synthesizing example are shown in FIG. 2.

As is clear from FIG. 2, in the condition that pH is adjusted at 12, the existing form of zinc oxide on iron oxide-coated titanium oxide coated mica is in an amorphous form of fine particle state.

Further, in this amorphous form, separated form of zinc oxide is not definitely recognized when the surface of the substrate is observed at 10,000 magnifications by using a scanning electron microscope (S-450, Hitachi).

Figure 3A:
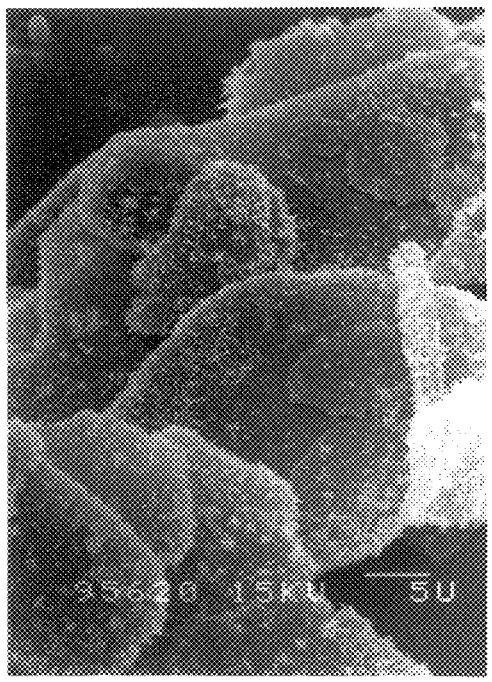
FIG. 3 contains microphotographs of acicular crystal of zinc oxide and iron oxide-coated titanium oxide coated mica, FIG. 3 (A) shows a whole particle and FIG. 3 (B) shows the surface state which is further magnified.
Figure 3B:
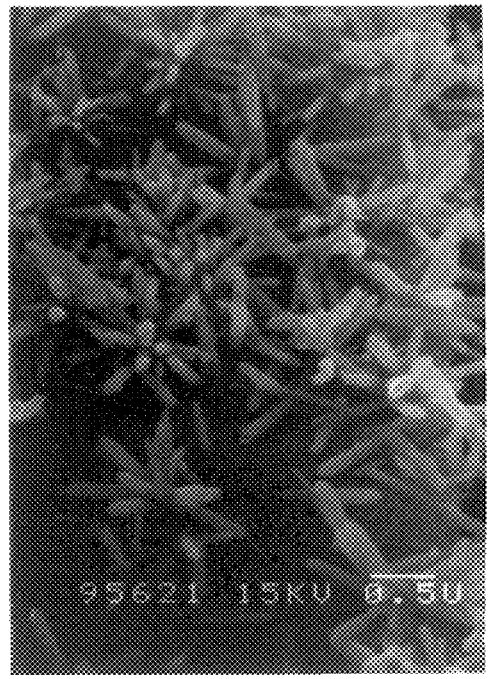

As compared with this, microphotographs of zinc oxide and iron oxide-coated titanium oxide coated mica obtained by adjusting pH of manufacturing time at 10 are shown in FIG. 3. As is clear from FIG. 3, the existing form of zinc oxide on iron oxide-coated titanium oxide coated mica is acicular crystal.

Fatty acid-solidifying ability of each zinc oxide and iron oxide-coated titanium oxide coated mica shown in FIG. 2 and FIG. 3 are also investigated. Amorphous state zinc oxide and iron oxide-coated titanium oxide coated mica shown in FIG. 2 shows excellent fatty acid-solidifying ability. On the contrary, acicular crystal zinc oxide and iron oxide-coated titanium oxide coated mica shows no fatty acid-solidifying ability at all.

As a result of the foregoing, the separation form needs to be in amorphous state so that zinc oxide can effectively display fatty acid-solidifying ability on the substrate such as iron oxide-coated titanium oxide coated mica.

The relationship of pH at manufacturing time, the crystal form of zinc oxide, and fatty acid-solidifying ability (the time passed 60 minutes) are shown in TABLE 1. In TABLE 1, zinc oxide is separated as acicular crystal and fatty acid-solidifying ability can not be observed where pH is less than 11.0. Where pH is 11.0 or more, the crystal form becomes amorphous state with excellent fatty acid-solidifying ability.

TABLE 1

| Testing examples | pH | Fatty acid-solidifying ability | Form of surface |
| --- | --- | --- | --- |
| 1 | 8 | X | Acicular |
| 2 | 10 | X | Acicular |
| 3 | 10.5 | X | Acicular |
| 4 | 11.0 | Δ | Acicular/Amorphous |
| 5 | 11.5 | ○ | Amorphous |
| 6 | 12.0 | ○ | Amorphous |
| 7 | 12.5 | ○ | Amorphous |

TABLE 1-continued

| Testing examples | pH | Fatty acid-solidifying ability | Form of surface |
|---|---|---|---|
| 8 | 13.0 | Δ | Amorphous |
| 9 | 13.5 | X | Uncoated |

X: no fatty acid-solidification ability; Δ: some fatty acid-solidification ability; ○: excellent fatty acid-solidification ability.

Coating of Zinc Oxide and Fatty Acid-Solidifying Ability

Next, the inventors conducted the tests of fatty acid-solidifying ability of zinc oxide and iron oxide-coated titanium oxide coated mica manufactured by said method and iron oxide-coated titanium oxide coated mica not coated with zinc oxide.

Figure 4:
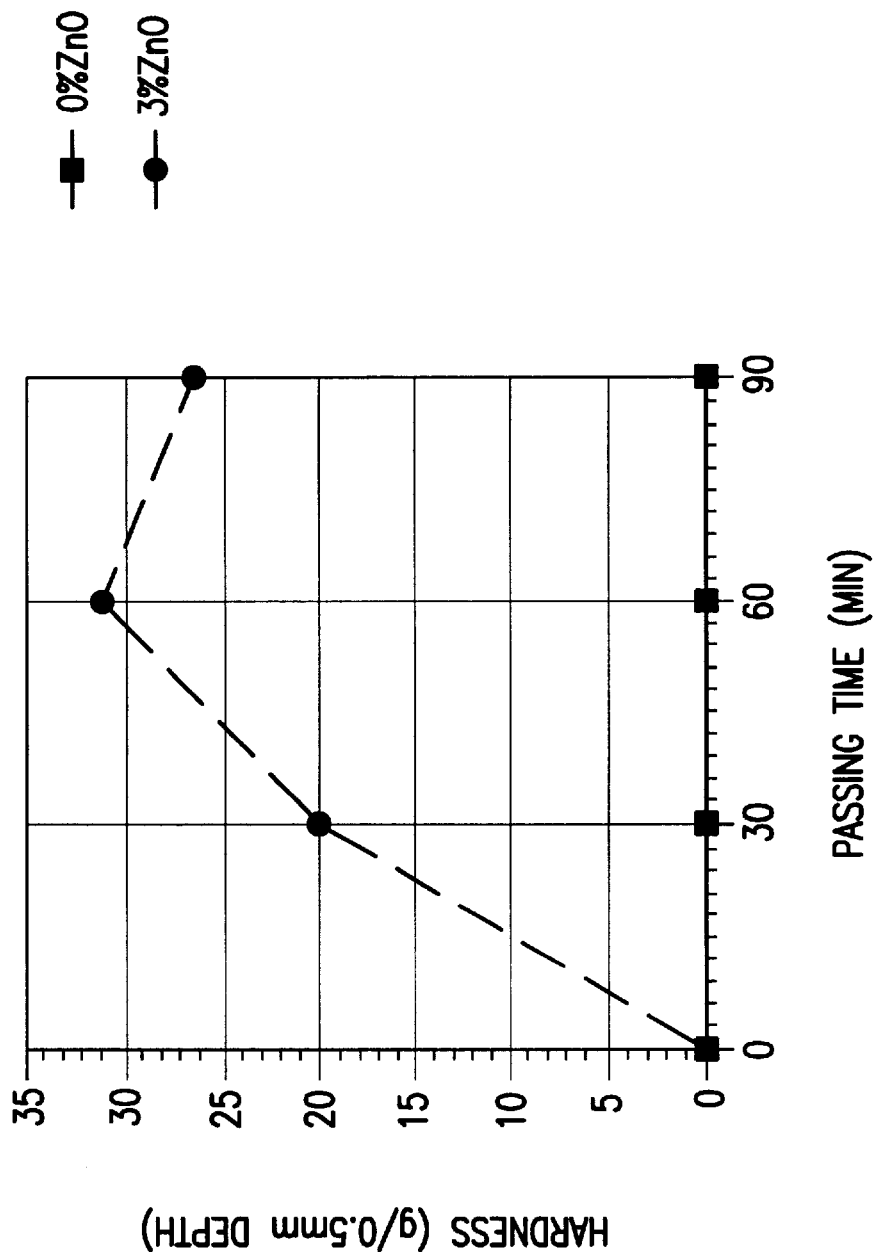
FIG. 4 is an explanatory view of the relationship between the coating of zinc oxide and fatty acid-solidifying ability.

This result is shown in FIG. 4.

As is clear from FIG. 4, excellent fatty acid-solidifying ability is displayed in the case where just 3% of zinc oxide is coated. On the other hand, fatty acid-solidifying ability is not displayed at all in the case where zinc oxide is not coated. It is appreciated that fatty acid-solidifying ability of the powder in accordance with the present invention is derived from zinc oxide.

Coating of Zinc Oxide and the Change of Color Tone

Next, the inventors studied the change of color tone of iron oxide-coated titanium oxide coated mica which was accompanied with coating of zinc oxide.

Namely, iron oxide-coated titanium oxide coated mica shows extremely bright red color due to the synergistic function of red color of iron oxide and red interference color of titanium oxide coated mica. Accordingly, the inventors proceeded with the study so that the bright red color of iron oxide-coated titanium oxide coated mica should not be spoiled by coating of zinc oxide.

Figure 5A:
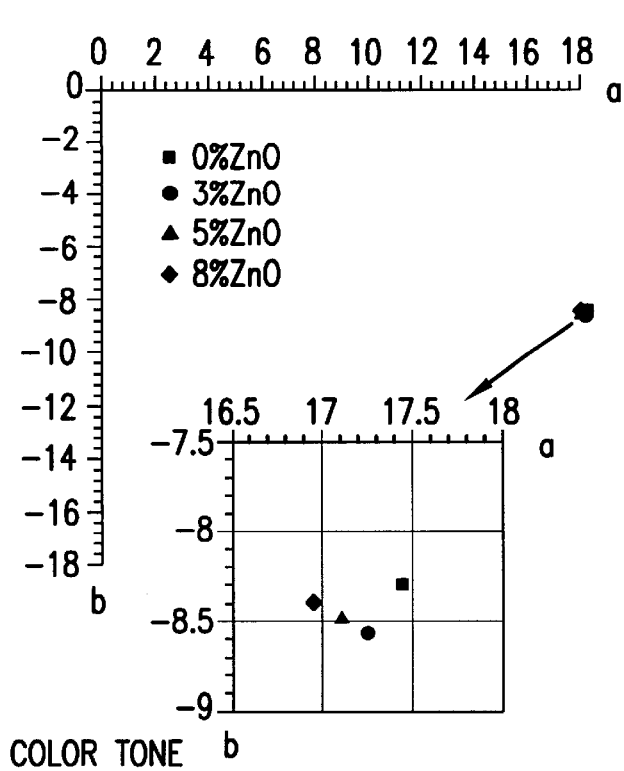
FIG. 5 is an explanatory view of the relationship between the amount of zinc oxide coated and the color tone of iron oxide-coated titanium oxide coated mica.
Figure 5B:
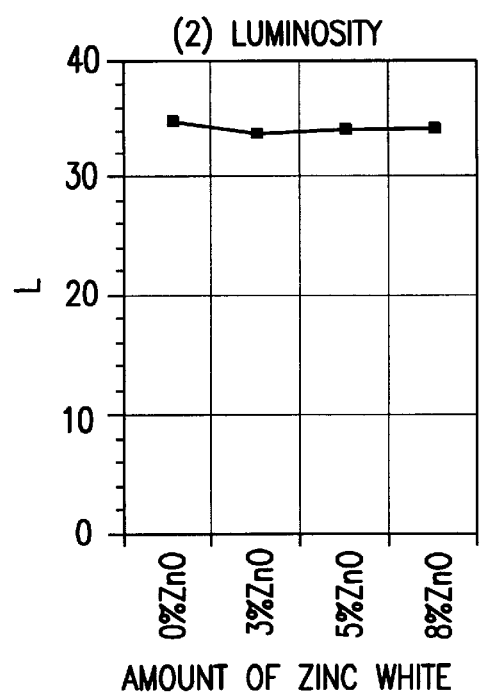
Figure 5C:
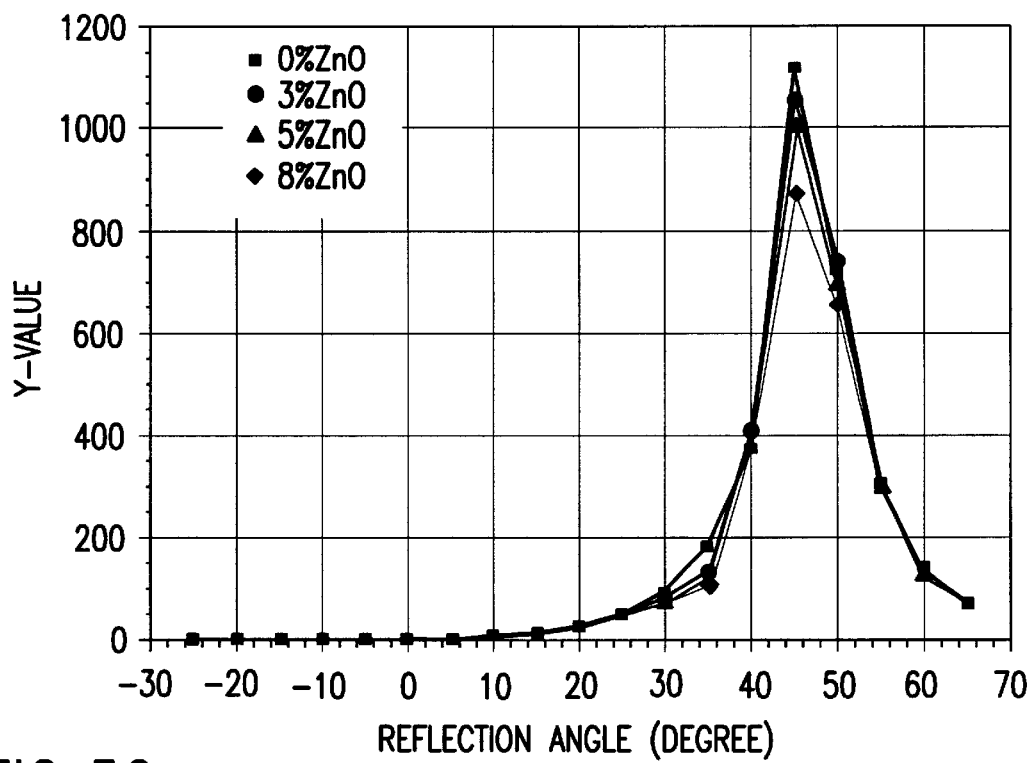

First, the inventors coated 3, 5, and 8% of zinc oxide on iron oxide-coated titanium oxide coated mica according to the above-mentioned manufacturing example to test the color tone, brilliance, and light luminance. FIG. 5 (A), (B), and (C) shows color tone, brilliance, and light luminance of each powder, respectively.

As is clear from FIG. 5, color tone, brilliance, and light luminance of iron oxide-coated titanium oxide coated mica shows no big difference in each coating amount of zinc oxide up to 8%.

Figure 6A:
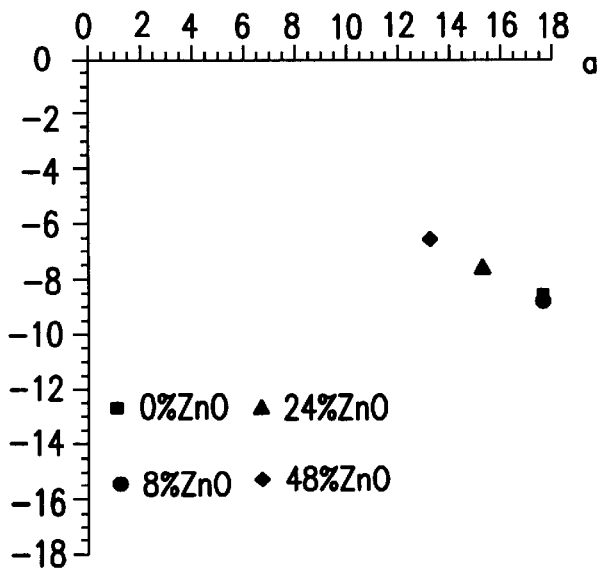
FIG. 6 is an explanatory view of the relationship between the amount of zinc oxide coated and the color tone of iron oxide-coated titanium oxide coated mica.
Figure 6B:
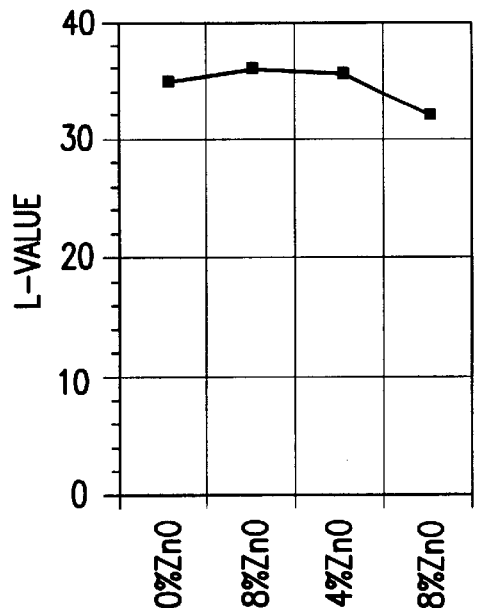
Figure 6C:
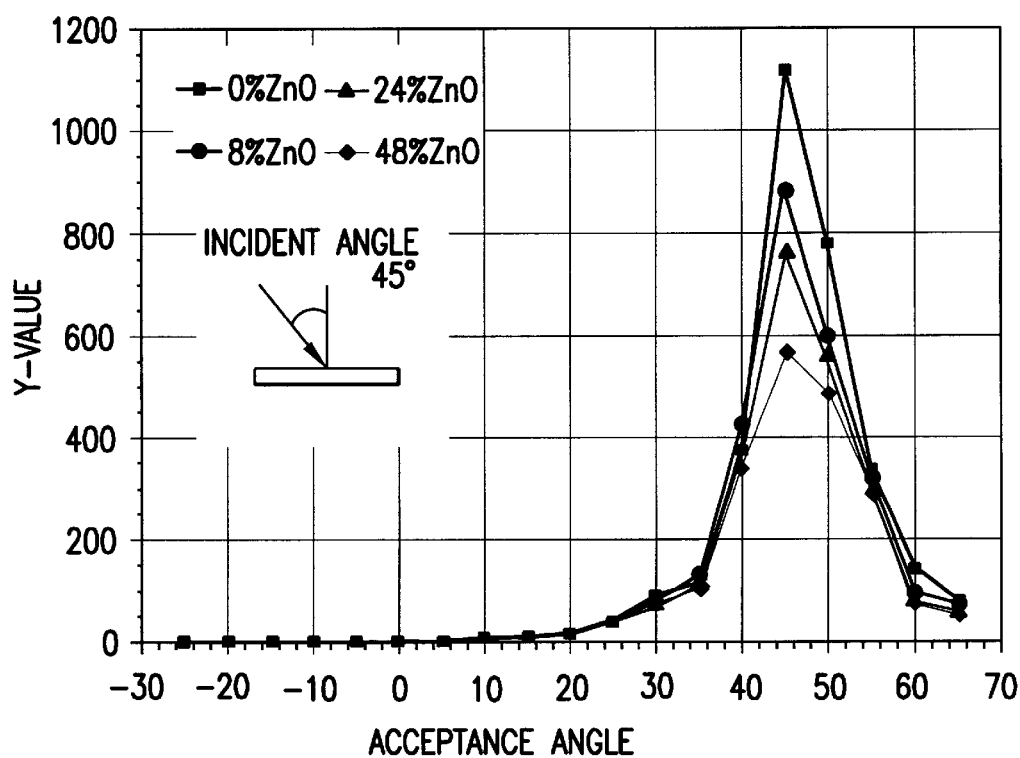

FIG. 6 shows the examples that iron oxide-coated titanium oxide coated mica coated with 24% and 48% of zinc oxide, respectively.

As is clear from FIG. 6, the change in color tone, brilliance, and light luminance can be hardly observed in the case where coating amount of zinc oxide is up to 8% by weight. However, color tone is clearly transferred to the direction of origin, and brilliance and light luminance are considerably lower in the case where 24% or 48% of zinc oxide is coated. Therefore, it is appreciated that color tone becomes dull and brightness is lower in the case where the coating amount of zinc oxide is largely exceeded 8%.

Accordingly, it is preferable that the coating amount of zinc oxide is 3 to 8% in order to display fatty acid-solidifying ability without giving bad influence on color tone of iron oxide-coated titanium oxide coated mica (substrate) coated with zinc oxide.

Next, powdery foundation was manufactured by conventional way using red zinc oxide-coated material (the coating amount of zinc oxide is 5.0%) which was manufactured according to the above-mentioned method The inventors studied the properties of the powdery foundation.

TABLE 2

| Powder | | | | | | | ...Total | 90.0% |
|---|---|---|---|---|---|---|---|---|
| Talc | 89.9 | 89.5 | 89.0 | 88.0 | 85.0 | 80.0 | 75.0 | 70.0 |
| Red zinc oxide coated material | 0.1 | 0.5 | 1.0 | 2.0 | 5.0 | 10.0 | 15.0 | 20.0 |
| Theoretical amount of the ingredients of red zinc oxide-coated material | | | | | | | | |
| Titanium oxide coated-mica coated iron oxide | 0.095 | 0.475 | 0.95 | 1.90 | 4.75 | 9.5 | 14.25 | 19.0 |
| Zinc | 0.005 | 0.025 | 0.05 | 0.10 | 0.25 | 0.5 | 0.75 | 1.0 |
| Binder | | | | | | | | |
| Squalane | | | | | | 6.0% | | |
| Octyldodecyl myristate | | | | | | 2.0 | | |
| Neopentyl glycol diisooctanoate | | | | | | 2.0 | | |
| Evaluation | | | | | | | | |
| spreadability | ○ | ○ | ○ | ○ | ○ | ○ | ○ | ○ |
| Fatty acid-solidifying ability | X | Δ | ○ | ○ | ○ | ○ | ○ | ○ |

X: no fatty acid-solidification ability;
Δ: some fatty acid-solidification ability;
○: excellent fatty acid-solidification ability.

X: no fatty acid-solidification ability; Δ: some fatty acid-solidification ability; ○: excellent fatty acid-solidification ability.

As is clear from TABLE 2, fatty acid-solidifying ability is observed in the case where the amount of zinc oxide-coated material is 0.5% (0.025% as the amount of zinc oxide). Also, fatty acid-solidifying ability is distinctively displayed in the case where the amount of zinc oxide-coated material is 1.0% (0.05% as the amount of zinc oxide). Further, spreadability can be maintained even when 20.0% of zinc oxide-coated material (1.0% as the amount of zinc) is compounded.

TABLE 3

| Powder | | | | | | | ...Total | 90.0% |
|---|---|---|---|---|---|---|---|---|
| Talc | 89.9 | 89.5 | 89.0 | 88.0 | 85.0 | 80.0 | 75.0 | 70.0 |
| Titanium oxide coated-mica coated iron oxide | 0.095 | 0.475 | 0.95 | 1.90 | 4.75 | 9.5 | 14.25 | 19.0 |
| Zinc white | 0.005 | 0.025 | 0.05 | 0.10 | 0.25 | 0.5 | 0.75 | 1.0 |
| Binder | | | | | | | | |
| Squalane | | | | | | 6.0% | | |
| Octyldodecyl myristate | | | | | | 2.0 | | |
| Neopentyl glycol diisooctanoate | | | | | | 2.0 | | |
| Evaluation | | | | | | | | |
| Sliding goodness | ○ | ○ | ○ | ○ | ○ | Δ | X | X |
| Fatty acid-solidifying ability | X | Δ | ○ | ○ | ○ | ○ | ○ | ○ |

X: no fatty acid-solidification ability;
Δ: some fatty acid-solidification ability;
○: excellent fatty acid-solidification ability.

X: no fatty acid-solidification ability; Δ: some fatty acid-solidification ability; ○: excellent fatty acid-solidification ability.

In TABLE 3, it is shown in the examples that iron oxide, and zinc white-coated titanium oxide coated mica, which are the ingredients of zinc oxide-coated material as shown in TABLE 2 are separately compounded.

When the fatty acid-solidifying ability is compared with the same amount of zinc oxide, there is not much difference in the case where zinc oxide is compounded as zinc oxide-coated material (TABLE 2) or zinc oxide (TABLE 3).

However, there is slight difficulty in sliding in the case where 0.5% of zinc oxide is compounded as zinc oxide. Sliding inferiority has been remarkably observed in the case where 1.0% or more of zinc oxide is compounded.

As described in the above, zinc oxide-coated material in the present embodiment can improve spreadability while maintaining fatty acid-solidifying ability of zinc.

In the following, more concrete manufacturing examples and compounding examples of zinc oxide-coated material are explained.

As for the compounding examples of mica coated zinc oxide, titanium oxide coated mica, and an external preparation for skin, application examples for the W/O foundation and the dual purpose foundation and their effects are explained below. The compounding forms of the present products are not limited to the following formulation.

The compositions of the W/O foundation shown in TABLE 4 are manufactured by the following process. These compositions are evaluated by the method described later. The evaluation items are listed according to TABLE 5. The results are collectively shown in TABLE 6.

TABLE 4

| Formulation | Examples | | | | Comp. Ex. |
| --- | --- | --- | --- | --- | --- |
|  | 1 | 2 | 3 | 4 | 1 |
| Decamethyl cyclopentasiloxane | 27.0 | 27.0 | 27.0 | 27.0 | 27.0 |
| Dimethylpolysiloxane | 3.0 | 3.0 | 3.0 | 3.0 | 3.0 |
| Polyoxyalkylene modified organopolysiloxane | 2.0 | 2.0 | 2.0 | 2.0 | 2.0 |
| 3% zinc oxide-coated mica processed with dextrin fatty acid ester | 0.2 | — | — | — | — |
| 3% zinc oxide-coated titanium oxide coated mica processed with dextrin fatty acid ester | — | 0.2 | — | — | — |
| 5% zinc oxide-coated titanium oxide coated mica processed with dextrin fatty acid ester | — | — | 0.2 | — | — |
| 8% zinc oxide-coated titanium oxide coated mica processed with dextrin fatty acid ester | — | — | — | 0.2 | — |
| Titanium oxide coated mica processed with dextrin fatty acid ester | — | — | — | — | 0.2 |
| Titanium dioxide processed with dextrin fatty acid ester | 4.0 | 4.0 | 4.0 | 4.0 | 4.0 |
| Iron oxide pigment processed with dextrin fatty acid ester | 2.0 | 2.0 | 2.0 | 2.0 | 2.0 |
| 1,3-Butylene glycol | 4.0 | 4.0 | 4.0 | 4.0 | 4.0 |
| Ion-exchanged water | Balance | Balance | Balance | Balance | Balance |

Evaluation Items

Each compounding example is evaluated as follows: For each example, a 5-person expert panel was assigned to it These 5 persons, after using the example product, gave their evaluations (grade 1 to 5) according to the evaluation items listed on TABLE 5. Their grades are based upon that the Comparative Example is regarded as 3.

TABLE 5

| Evaluation Items | Grade | | | | |
| --- | --- | --- | --- | --- | --- |
|  | 1 | 2 | 3 | 4 | 5 |
| Cosmetic durability | Bad←→ Good | | | | |
| Spreadability | Bad←→ Good | | | | |
| Natural brightness of skin | Unnatural←→ Natural | | | | |
| Conspicuousness of unevenness and somberness | Conspicuous←→ Inconspicuous | | | | |
| Beautifulness in finishing | Unbeautiful←→ Beautiful | | | | |

Evaluation Results

TABLE 6

| Evaluation Items | Examples | | | | Comp. Ex. |
| --- | --- | --- | --- | --- | --- |
|  | 1 | 2 | 3 | 4 | 1 |
| Cosmetic durability | 3.8 | 3.8 | 3.8 | 4.2 | 3.0 |
| Spreadability | 3.2 | 3.2 | 2.8 | 2.6 | 3.0 |
| Natural brightness of skin | 4.2 | 3.4 | 3.6 | 3.6 | 3.0 |
| Conspicuousness of unevenness and somberness | 4.0 | 2.4 | 3.6 | 3.2 | 3.0 |
| Beautifulness in finishing | 4.2 | 3.6 | 3.4 | 3.0 | 3.0 |

It is understood that examples 1 to 4, which were coated with zinc oxide, have higher cosmetic durability, according to the evaluation results of TABLE 6. The increase in the cosmetic durability effect is relative to the increase in the amount of coating zinc oxide. Although the spreadability of examples is slight bad, the spreadability can be sufficiently acceptable, particularly in the case where the coating amount of zinc oxide is in the range of 3 to 8% by weight. It is appreciated that unnatural brightness of skin which is the difficulty in case of compounding titanium oxide coated mica with the foundation, is recognized as natural brightness. Because unnatural brightness of the skin is lessened by coating of zinc oxide. In addition, in examples 2 to 4, it appears that zinc oxide coating contributes to a hiding effect which would revive the unevenness and somberness caused by the interference effect of titanium oxide coated mica. In sum, the inventors of the present case recognize that in cases where 3 to 8% of zinc oxide is coated on titanium oxide coated mica, these W/O foundations show good spreadability and cosmetic durability, are capable of hiding unevenness and somberness, and demonstrate beautifuilness in finishing.

Examples 5 to 8 show the compounding examples in the dual purpose foundation. The evaluation is the same as in the case of the W/O foundation.

TABLE 7

Formulation in examples of the dual purpose foundations (Parts by weight)

| Formulation | Examples | | | | Comp. Ex. |
| --- | --- | --- | --- | --- | --- |
|  | 5 | 6 | 7 | 8 | 2 |
| Mica processed with silicone | 40.0 | 40.0 | 40.0 | 40.0 | 40.0 |
| Talc processed with silicone | 15.0 | 15.0 | 15.0 | 15.0 | 15.0 |
| Globular resin powder processed with silicone | 10.0 | 10.0 | 10.0 | 10.0 | 10.0 |
| Red iron oxide processed with silicone | 0.6 | 0.6 | 0.6 | 0.6 | 0.6 |
| Yellow iron oxide processed with silicone | 1.0 | 1.0 | 1.0 | 1.0 | 1.0 |
| Black iron oxide processed with | 0.1 | 0.1 | 0.1 | 0.1 | 0.1 |

TABLE 7-continued

Formulation in examples of the dual purpose foundations (Parts by weight)

| Formulation | Examples 5 | 6 | 7 | 8 | Comp. Ex. 2 |
|---|---|---|---|---|---|
| silicone | | | | | |
| Titanium dioxide processed with silicone | 10.0 | 10.0 | 10.0 | 10.0 | 10.0 |
| Titanium oxide coated mica processed with silicone | 15.0 | — | — | — | — |
| 3% zinc oxide-coated mica processed with silicone | — | 15.0 | — | — | — |
| 5% zinc oxide-coated titanium oxide coated mica processed with silicone | — | — | 15.0 | — | — |
| 8% zinc oxide-coated titanium oxide coated mica processed with silicone | — | — | — | 15.0 | — |
| Titanium oxide coated mica processed with silicone | — | — | — | — | 15.0 |
| Paraben | q.s. | q.s. | q.s. | q.s. | q.s. |
| Dimethylpolysiloxane | 3.0 | 3.0 | 3.0 | 3.0 | 3.0 |
| Liquid paraffin | 4.0 | 4.0 | 4.0 | 4.0 | 4.0 |
| Methylphenyl polysiloxane | 3.0 | 3.0 | 3.0 | 3.0 | 3.0 |
| Petrolatum | 3.0 | 3.0 | 3.0 | 3.0 | 3.0 |
| Antioxidant | q.s. | q.s. | q.s. | q.s. | q.s. |

TABLE 8

Evaluation results of the dual purpose foundations

| Evaluation Item | Examples 5 | 6 | 7 | 8 | Comp. Ex. 2 |
|---|---|---|---|---|---|
| Cosmetic durability | 3.6 | 3.6 | 3.8 | 4.2 | 3.0 |
| Spreadability | 3.0 | 3.0 | 2.8 | 2.6 | 3.0 |
| Natural brightness of skin | 2.8 | 3.8 | 3.8 | 3.4 | 3.0 |
| Conspicuousness of unevenness and somberness | 2.4 | 3.6 | 3.4 | 3.2 | 3.0 |
| Beautifulness in finishing | 4.2 | 3.4 | 3.4 | 3.0 | 3.0 |

It is understood that examples 6 to 8, which were coated with zinc oxide, have -higher cosmetic durability, according to the evaluation results of TABLE 8. The increase in the cosmetic durably effect is relative to the increase in the amount of coating zinc oxide. Although the spreadability of examples is slight bad, the spreadability can be sufficiently acceptable, particularly in the case where the coating amount of zinc oxide is in the range of 3 to 8% by weight. It is appreciated that unnatural brightness of skin which is the difficulty in case of compounding titanium oxide coated pica with the foundation, is recognized as natural brightness, Because unnatural brightness of the skin is lessened by coating of zinc oxide. In addition, in examples 5 to 8, it appears that zinc oxide coating contributes to a hiding effect which would revive the unevenness and somberness caused by the interference effect of titanium oxide coated mica. In sum, the inventors of the present case recognize that in cases where 3 to 8% of zinc oxide is coated on titanium oxide coated mica, these dual purpose foundations show good spreadability and cosmetic durability, are capable of hiding unevenness and somberness, and demonstrate beautifuilness in finishing.

Examples 9 to 12 show the compounding examples in the powdery foundations. The evaluation is the same as in the case of the W/O foundation.

TABLE 9

Formulation in examples of the powdery foundations (Parts by weight)

| Formulation | Examples 9 | 10 | 11 | 12 | Comp. Ex. 3 |
|---|---|---|---|---|---|
| Mica processed with silicone | 23.0 | 23.0 | 23.0 | 23.0 | 23.0 |
| Talc processed with silicone | 20.3 | 20.3 | 20.3 | 20.3 | 20.3 |
| Kaolin | 10.0 | 10.0 | 10.0 | 10.0 | 10.0 |
| Nylon powder | 10.0 | 10.0 | 10.0 | 10.0 | 10.0 |
| Iron oxide | 1.0 | 1.0 | 1.0 | 1.0 | 1.0 |
| Yellow iron oxide processed with silicone | 3.0 | 3.0 | 3.0 | 3.0 | 3.0 |
| Black iron oxide processed with silicone | 0.2 | 0.2 | 0.2 | 0.2 | 0.2 |
| Titanium dioxide | 10.0 | 10.0 | 10.0 | 10.0 | 10.0 |
| 3% zinc oxide-coated mica processed with silicone | 15.0 | — | — | — | — |
| 3% zinc oxide-coated titanium oxide coated mica processed with silicone | — | 15.0 | — | — | — |
| 5% zinc oxide-coated titanium oxide coated mica processed with silicone | — | — | 15.0 | — | — |
| 8% zinc oxide-coated titanium oxide coated mica processed with silicone | — | — | — | 15.0 | — |
| Titanium oxide coated mica processed with silicone | — | — | — | — | 15.0 |
| Squalane | 6.0 | 6.0 | 6.0 | 6.0 | 6.0 |
| Lanolin acetate | 1.0 | 1.0 | 1.0 | 1.0 | 1.0 |
| Otyldodecyl myristate | 2.0 | 2.0 | 2.0 | 2.0 | 2.0 |
| Neopentyl glycol diisooctanoate | 2.0 | 2.0 | 2.0 | 2.0 | 2.0 |
| Sorbitan monooleate | 0.5 | 0.5 | 0.5 | 0.5 | 0.5 |
| Other ingredients (antioxidant, antiseptic, perfume) | q.s. | q.s. | q.s. | q.s. | q.s. |

TABLE 10

Evaluation results of the powdery foundation

| Evaluation Item | Examples 9 | 10 | 11 | 12 | Comp. Ex. 3 |
|---|---|---|---|---|---|
| Cosmetic durability | 3.6 | 3.6 | 3.8 | 4.2 | 3.0 |
| Spreadability | 3.0 | 3.0 | 2.8 | 2.6 | 3.0 |
| Natural brightness of skin | 2.8 | 3.8 | 3.8 | 3.4 | 3.0 |
| Conspicuousness of unevenness and somberness | 2.4 | 3.6 | 3.4 | 3.2 | 3.0 |
| Beautifulness in finishing | 4.2 | 3.4 | 3.4 | 3.0 | 3.0 |

It is understood that examples 9 to 12, which were coated with zinc oxide, have higher cosmetic durability, according to the evaluation results of TABLE 10. The increase in the cosmetic durability effect is relative to the increase in the amount of coating zinc oxide. Although the spreadability of examples is slight bad, the spreadability can be sufficiently acceptable, particularly in the case where the coating amount of zinc oxide is in the range of 3 to 8% by weight. It is appreciated that unnatural brightness of skin which is the difficulty in case of compounding titanium oxide coated mica with the foundation, is recognized as natural brightness. Because unnatural brightness of the skin is lessened by coating of zinc oxide. In addition, in examples 9 to 12, it appears that zinc oxide coating contributes to a hiding effect which would revive the unevenness and somberness caused by the interference effect of titanium oxide coated mica. In sum, the inventors of the present case recognize that in cases where 3 to 8% of zinc oxide is coated on titanium oxide coated mica, these powdery foundations show good spreadability and cosmetic durability, are capable of hiding unevenness and somberness, and demonstrate beautifulness in finishing.

In sum, as described above, a zinc oxide-coated material of the present invention is capable of forming a coated material without spoiling fatty acid-solidifying ability of zinc oxide, since the crystal form of zinc oxide is in an amorphous state.

What is claimed is:

1. The zinc oxide-coated material comprising an amorphous state of zinc oxide coated on a substrate, wherein the substrate is a flake.

2. The zinc-oxide coated material according to claim 1, wherein the flake is mica.

3. The zinc oxide-coated material according to claim 1, wherein the flake is titanium oxide coated mica.

4. The red zinc oxide-coated material according to claim 1, wherein the flake is an iron oxide-coated titanium oxide coated mica.

5. The zinc oxide-coated material comprising an amorphous state of zinc oxide coated on a substrate, wherein the amount of zinc oxide is in the range of 1 to 8% by weight.

6. A fatty acid-solidifying powder comprising an amorphous state of zinc oxide-coated material.

7. An external preparation for skin comprising the fatty acid-solidifying powder of claim 6.

8. The fatty acid-solidifying powder according to claim 6, wherein said zinc oxide-coated material is a flake.

9. The fatty acid-solidifying powder according to claim 8, wherein said flake is mica.

10. The fatty acid-solidifying powder according to claim 8, wherein said flake is mica and a titanate.

11. The fatty acid-solidifying powder according to claim 8, wherein said flake is an iron oxide-coated mica containing a titanate.

12. The fatty acid-solidifying powder according to claim 6, wherein said zinc oxide is in the range of 1 to 8% by weight.

13. The zinc oxide-coated material according to claim 4, wherein said zinc oxide-coated material is red.

* * * * *